United States Patent [19]
Marion et al.

[11] Patent Number: 5,994,594
[45] Date of Patent: Nov. 30, 1999

[54] PROCESS FOR PRODUCING AN ALPHA OLEFIN, A TERTIARY OLEFIN AND/OR AN ETHER FROM AN UNSATURATED HYDROCARBON CUT

[75] Inventors: Marie-Claire Marion, Villeurbanne; Vincent Coupard, Lyons; Alain Forestiere, Vernaison; Philippe Travers, Rueil Malmaison; Jean-Charles Viltard, Valence, all of France

[73] Assignee: Institut Francais du Petrole, Rueil-Malmaison, France

[21] Appl. No.: 09/053,061

[22] Filed: Apr. 1, 1998

[30] Foreign Application Priority Data

Apr. 2, 1997 [FR] France .................................. 97 04117

[51] Int. Cl.[6] .............................. C07C 41/00; C07C 9/00; C07C 2/00; C07C 7/00
[52] U.S. Cl. ............................ 568/579; 585/16; 585/500; 585/800
[58] Field of Search .............................. 568/579; 585/16, 585/500, 800

[56] References Cited

U.S. PATENT DOCUMENTS 4,447,668  5/1984  Smith, Jr. et al. ........................ 585/639
5,567,860  10/1996  Mowry et al. ........................... 585/639

FOREIGN PATENT DOCUMENTS 0869107  10/1998  European Pat. Off. .
2 527 201  11/1983  France .

Primary Examiner—Louise N. Leary
Attorney, Agent, or Firm—Millen, White, Zelano & Branigan, P.C.

[57] ABSTRACT

A process for producing an alpha olefin, a tertiary olefin or a tertiary alkyl ether from an unsaturated hydrocarbon cut containing at least one alpha olefin and at least one etherifiable tertiary olefin comprises synthesising at least one tertiary alkyl ether to obtain a product which is separated into a fraction (O1) which is depleted in ether and containing the alpha olefin and a fraction (E1) which is enriched in ether, followed by decomposition of at least a portion of the ether in fraction (E1) into a product (P1) containing at least one alcohol and at least one tertiary olefin, which is fractionated in a fractionation zone (C5) into a fraction (B1) containing the major portion of the tertiary olefin and a fraction (A1) containing the major portion of the alcohol.

18 Claims, 5 Drawing Sheets

PROCESS FOR PRODUCING AN ALPHA OLEFIN, A TERTIARY OLEFIN AND/OR AN ETHER FROM AN UNSATURATED HYDROCARBON CUT

The invention concerns an integrated process for synthesising a pure alpha olefin, a pure tertiary olefin and possibly a tertiary alkyl ether from at least one unsaturated hydrocarbon cut containing at least one alpha olefin and at least one etherifiable tertiary olefin; it comprises a step for etherification of the hydrocarbon cut by at least one alcohol in which a product is formed comprising at least one tertiary alkyl ether which is sent to a separation zone from which a hydrocarbon fraction which is depleted in tertiary alkyl ether and containing the alpha olefin is recovered and at least a portion of a fraction which is enriched in tertiary alkyl ether is optionally recovered, and the other portion, or all of it, is sent to a tertiary alkyl ether decomposition zone from which a product comprising at least one high purity tertiary olefin is recovered.

In particular, the invention concerns a process for the production of high purity 1-butene, high purity isobutene and preferably methyl-tertio-butyl-ether (MTBE) from a $C_4$ hydrocarbon cut containing 1-butene and isobutene, comprising forming a product containing MTBE from this cut and methanol, then separating from this product a hydrocarbon fraction which is depleted in MTBE containing the 1-butene and a fraction which is enriched in MTBE at least a portion of which is optionally recovered and the other portion, or all, is sent to a MTBE decomposition zone from which a product comprising methanol and isobutene is recovered which is sent to a fractionation zone from which a product which is enriched in methyl alcohol is obtained, which may be recycled to the MTBE synthesis stage, and a product which is enriched in purified isobutene is recovered. The remainder of the description of the present invention, in particular the operating conditions, is given by way of indication for the synthesis of isobutene from hydrocarbon cuts comprising essentially hydrocarbons containing 4 carbon atoms (among them 1-butene and isobutene) by synthesis and decomposition of MTBE. The process of the present invention is also applicable to the synthesis of other tertiary olefins and to recovery of other alpha olefin(s) from other hydrocarbon cut(s) containing such olefins. The process of the present invention comprises a step for synthesising at least one tertiary alkyl ether (for example ETBE (ethyl-tertio-butyl-ether), ETAE (ethyl-tertio-amyl-ether), TAME (tertio-amyl-methyl-ether), isopropyl-tertio-butyl-ether), and its decomposition.

In the current context of reformulated gasoline, the production of ethers such as MTBE, ETBE or TAME to increase the octane index continues to increase. Further, in the chemicals and petrochemicals industry and in particular in the polymer industry (polyisobutene, special polyethylenes...) the need for olefins, in particular for high purity isobutene and 1-butene, are also increasing. However, isobutene and 1-butene have very similar boiling points (−6.9° C. and −6.3° C. respectively) and cannot readily be separated by simple distillation.

One method of readily separating 1-butene from isobutene is to selectively transform the isobutene into an ether, for example MTBE or ETBE. The etherification step thus isolates the isobutene in the form of a tertiary alkyl ether. Using the reverse, ether decomposition, reaction, a (very) high purity isobutene can then be produced. In that scheme, and provided that the isobutene has been thoroughly etherified, very high purity 1-butene can be produced.

High purity isobutene production from cracking MTBE is as suitable for small capacities as for large capacities. Further, such a route benefits from the infrastructure generated by the increasing importance of ethers in reformulated gasoline. A number of refineries throughout the world have MTBE production installations, for example. Further, there is a global exchange market for MTBE. This means that the production of high purity isobutene from MTBE can readily be carried out anywhere in the world, in and remote from refineries.

The concept of producing isobutene by decomposing an ether, more particularly MTBE, has long been known, but prior art processes have suffered from certain disadvantages.

In the process developed by SUMITOMO described, for example, in European patent application EP-A-0,068,785, the MTBE decomposition reaction is carried out in the liquid phase, in the presence of a solid acid catalyst which is an ion exchange resin. Two product streams are obtained: isobutene and methanol. As described, isobutene is obtained directly overhead from a distillation column with no other purification step. The isobutene obtained contains a certain number of impurities, beginning with a small fraction of methanol which is azeotropically distilled from dimethylether (DME), which is a volatile compound formed by condensing methanol in the presence of an acid catalyst. It is probable that the purity of the isobutene is insufficient for use in the production of polyisobutene or other copolymers. Further, there is no apparent way of avoiding the accumulation of heavy impurities such as dimers of isobutene or methyl sec-butyl ether (MSBE), which in the long run results in a fatal reduction of product purity.

In the process developed by ERDOLCHEMIE, described in U.S. Pat. No. 4,409,421, for example, isobutene is purified by eliminating residual alcohol entrained with the tertiary olefin by adsorption. This method has the disadvantage of requiring regular regeneration of the adsorbent. Further, the problem of recovering the major portion of the alcohol from the decomposition step is not solved.

More recently in U.S. Pat. No. 5,095,164, the same company has described carrying out the decomposition reaction in a distillation apparatus. The catalyst is placed in the bottom of the column at the reboiler level. That particular implementation limits the reaction temperature, which is directly imposed by the nature of the ether and the operating pressure. Further. it apparently encourages the formation of reaction by-products such as the formation of dimers of isobutene and/or dimethylether formation. In this regard, the quality and/or development of the products is not clearly explained. In U.S. Pat. No. 4,287,379, BASF describes a scheme which integrates both ether synthesis, its separation then the ether decomposition step to produce the isobutene. However, in order to avoid certain purification steps, etherification is carried out with a $C_3$ or $C_4$ alcohol, which is a major disadvantage as regards the international MTBE market.

We can also cite the two flowcharts of the SNAMPROGETTI process presented in "Chemical Economy & Engineering Review", vol. 14, n° Jun. 6, 1982, including both an MTBE synthesis step and an MTBE decomposition step for the production of isobutene. However, such schemes do not provide for recovery of alpha olefins, in particular the production of high purity 1-butene.

U.S. Pat. No. 4,324,924 describes a process comprising the synthesis of MTBE from a $C_4$ cut containing isobutene and 1-butene comprising separating the product from the etherification reactor into a fraction comprising MTBE and a fraction containing unconverted hydrocarbons and methanol which is then sent to a second etherification reactor before being split into a fraction containing methanol and an essentially hydrocarbon fraction which is washed to eliminate traces of methanol contained therein, which are recovered. That process does not include simultaneous production of high purity isobutene and high purity 1-butene. Further, it is difficult to carry out as it involves the presence of an intermediate etherification reactor between two distillation zones with no real control of the alcohol/tertiary olefin stoichiometry at the inlet to the second reactor.

U.S. Pat. No. 4,797,133 describes a process for recovering high purity 1-butene from a $C_4$ cut containing it and also containing isobutene. That process comprises etherification of the isobutene, separating the product from the etherification zone into a fraction which is enriched in MTBE and into a fraction which is depleted in MTBE containing 1-butene. The latter fraction is sent to a water washing zone from which a fraction which is depleted in methanol containing 1-butene is obtained which is sent to a distillation column from which high purity 1-butene is obtained. Part of the fraction containing MTBE is sent to an alkylation zone or part is sent to gasoline pools. The process does not comprise simultaneous production of high purity isobutene and high purity 1-butene.

The process of the invention can overcome the disadvantages of the systems cited above. It concerns an integrated process for the production of high purity alpha olefin(s), tertiary olefin(s) characterized by a very high purity, and usually also tertiary alkyl ether(s), from a hydrocarbon cut containing at least one alpha olefin and at least one etherifiable tertiary olefin, by a method comprising forming then decomposing a tertiary alkyl ether. The process is thus also a process which is suitable for upgrading tertiary olefins and alpha olefins contained in hydrocarbon cuts in the form of purified alpha olefins, purified tertiary olefins, and/or tertiary alkyl ethers. The olefins are particularly for use in forming polymers and/or copolymers. The tertiary alkyl ethers are particularly for use as additives for internal combustion engine fuels.

The invention concerns a process comprising synthesising tertiary alkyl ether(s), in particular MTBE or ETBE, and decomposing at least a portion of these tertiary alkyl ether (s), in particular MTBE or ETBE, to produce high purity tertiary olefin(s), in particular isobutene. When decomposing other ethers, a mixture can be obtained which contains a plurality of tertiary olefins. Thus in the case of TAME decomposition, a mixture containing 2-methyl-1-butene and 2-methyl-2-butene is obtained.

In addition to the reaction zones themselves, the process of the invention comprises zones for purification, recovery or recycling the various products to optimise upgrading of the products used and to minimise losses.

The process of the present invention can include a variety of variations which can in particular improve the quality of the recovered tertiary olefin and which are described below. These variations can be implemented separately or simultaneously, either in their entirety or in combinations of two or more.

BRIEF DESCRIPTION OF DRAWINGS

FIGS. 1 to 5 are flowcharts each illustrating one of the multiple variations of the process of the present invention. The dotted lines show the various possible options, namely recycling options and optional apparatus in the variation under consideration. The present invention is described with reference to these figures with the aim of facilitating comprehension. In the figures, similar means are designated by the same reference letters and numbers. FIG. 1 illustrates the most general form of the process of the invention and is described below.

The present invention concerns a process for the production of a pure alpha olefin, a pure tertiary olefin and possibly a pure tertiary alkyl ether from an unsaturated hydrocarbon cut containing at least one alpha olefin and at least one etherifiable tertiary olefin, the process being characterized in that it comprises:

a) a step for forming at least one tertiary alkyl ether by bringing at least one unsaturated hydrocarbon cut containing at least one alpha olefin and at least one etherifiable tertiary olefin into contact with at least one alcohol, generally a primary or secondary alcohol generally containing 1 to 6, preferably 1 to 4, carbon atoms per molecule, generally a primary or secondary alcohol, preferably a primary alcohol, preferably methyl alcohol or ethyl alcohol or isopropanol, more preferably methyl alcohol or ethyl alcohol, in a reaction zone (R1) generally comprising at least one reactor and containing an etherification catalyst, generally under conditions for transforming at least a portion of the tertiary olefin into a tertiary alkyl ether;

b) a step for fractionating the major portion of the product from step a) in a fractionation zone (C1) to obtain an organic fraction (O1) which is depleted in tertiary alkyl ether, preferably containing practically no tertiary alkyl ether, and containing the alpha olefin (for example 1-butene) and an organic fraction (E1), enriched in the tertiary alkyl ether formed during step a), preferably containing practically all of said tertiary alkyl ether;

c) a step for decomposing at least a portion of the tertiary alkyl ether contained in the organic fraction (E1) from step b), in a reaction zone (R2) generally comprising at least one reactor and containing a catalyst for decomposing said ether, said step being carried out under conditions which enable at least partial decomposition of said tertiary alkyl ether into a product (P1) containing at least one alcohol and at least one tertiary olefin; and d) a step for fractionating at least a portion of product (P1) from step c), in a fractionation zone (C5) to obtain a fraction (B1) containing the major portion of the tertiary olefin and a minor fraction of alcohol and possibly light compounds which may be initially contained in said portion of product (P1), and into a fraction (A1) containing the major portion of the alcohol formed in step c), possibly ether which has not decomposed in step c) and possibly heavy compounds initially contained in said portion of product (P1).

The hydrocarbon cuts used in the present invention contain at least one tertiary olefin, at least one alpha olefin and in general other saturated or unsaturated hydrocarbons such as other olefins (for example linear olefins), paraffins (linear or branched), possibly a small proportion of water, and/or oxides of carbon. Olefins which can be prepared using the present invention are: for purified tertiary olefins, compounds in which one carbon atom of the olefinic bond is branched; and for purified alpha olefins, linear compounds in which one carbon atom of the olefinic bond is a terminal atom. These compounds normally contain 4 to 10 carbon atoms per molecule, preferably 4 to 8 carbon atoms per molecule and usually 4 to 6 carbon atoms per molecule. Examples of tertiary olefins are isobutene, 2-methyl-1-butene, 2-methyl-2-butene, tertiary hexenes, tertiary octenes and tertiary decenes. $C_4$ and/or $C_5$ cuts from refining or petrochemistry, $C_4$ and/or $C_5$ steam cracking cuts, normally after diene extraction, $C_4$ and/or $C_5$ catalytic cracking cuts, cuts from isomerisation (hydroisomerisation and skeletal isomerisation), and cuts obtained by dehydrogenation of paraffins can be cited.

Figure 1:
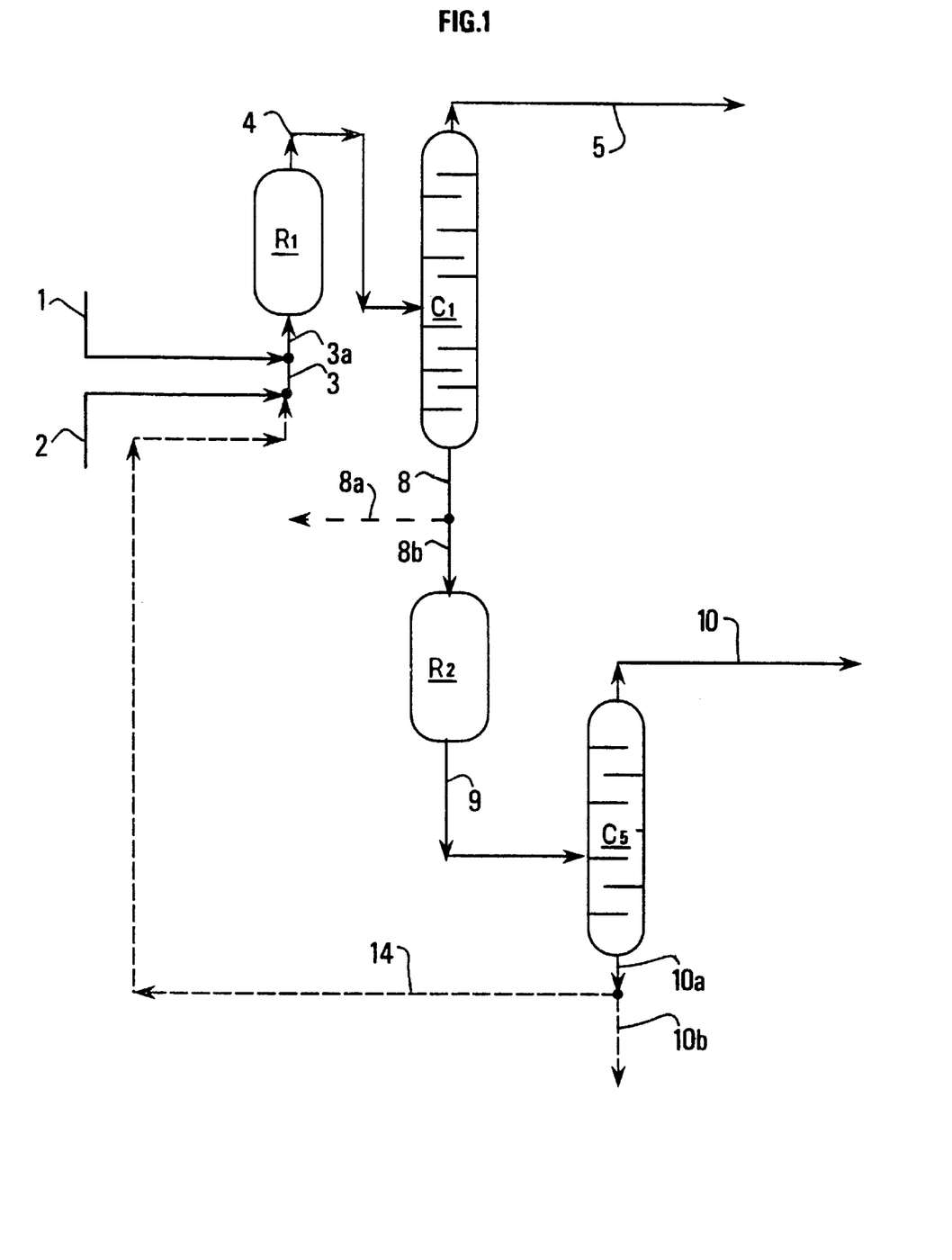
Figure 4:
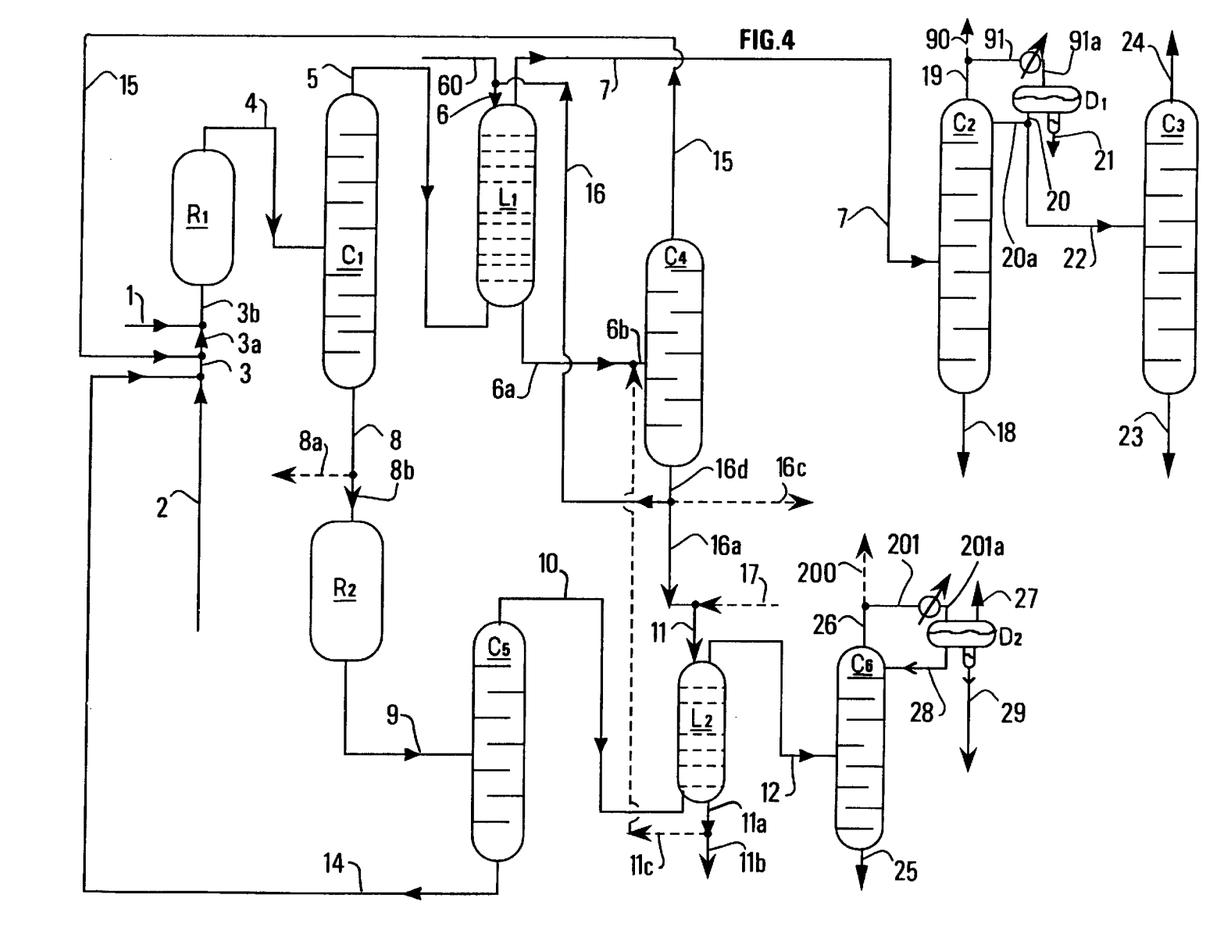

In a particular implementation of the process of the invention, a portion of the organic fraction (E1) containing the tertiary alkyl ether can be sent to the motor fuel pool and the other portion can be sent to ether decomposition step c). This implementation of the present invention is particularly illustrated in FIGS. 1 and 4 (line 8a). Regarding FIG. 1, the hydrocarbon feed containing at least one alpha olefin and at least one tertiary olefin is introduced into etherification zone R1 via lines 1 and 3a. An alcohol makeup is also introduced into zone R1 via lines 2, 3 and 3a and recycled alcohol is optionally introduced via lines 14, 3 and 3a. This zone contains an acid etherification catalyst. The product obtained by etherification of the hydrocarbon cut is sent to a fractionation zone (C1) via line 4 to obtain an organic fraction (O1) which is depleted in tertiary alkyl ether and contains the desired 1-butene which is recovered via line 5, and an organic fraction (E1) containing the ether which is formed which leaves via line 8. A portion of fraction (E1) is sent to the motor fuel pool via line 8a and the other portion is sent to ether decomposition zone (R2) via line 8b. A product (P1) containing at least one tertiary olefin, at least one alcohol, possibly ether which has not decomposed in step c), possibly light compounds and possibly heavy compounds, is recovered via line 9, and a portion of this product (P1), preferably the major portion, is sent via line 9 to fractionation zone (C5) from which a fraction (B1) containing the major portion of the tertiary olefin, possibly a minor fraction of alcohol and possibly light compounds initially contained in the portion of the product is obtained via line 10 while a fraction (A1) containing the major portion of the alcohol formed in step c), possibly ether which has not decomposed in step c) and possibly heavy compounds initially contained in that portion of product (P1) is obtained via line 10a. At least a portion of fraction (A1) can be recycled to reactor (R1) via lines 14, 3 and 3a or it can be evacuated via lines 10a and 10b.

Figure 2:
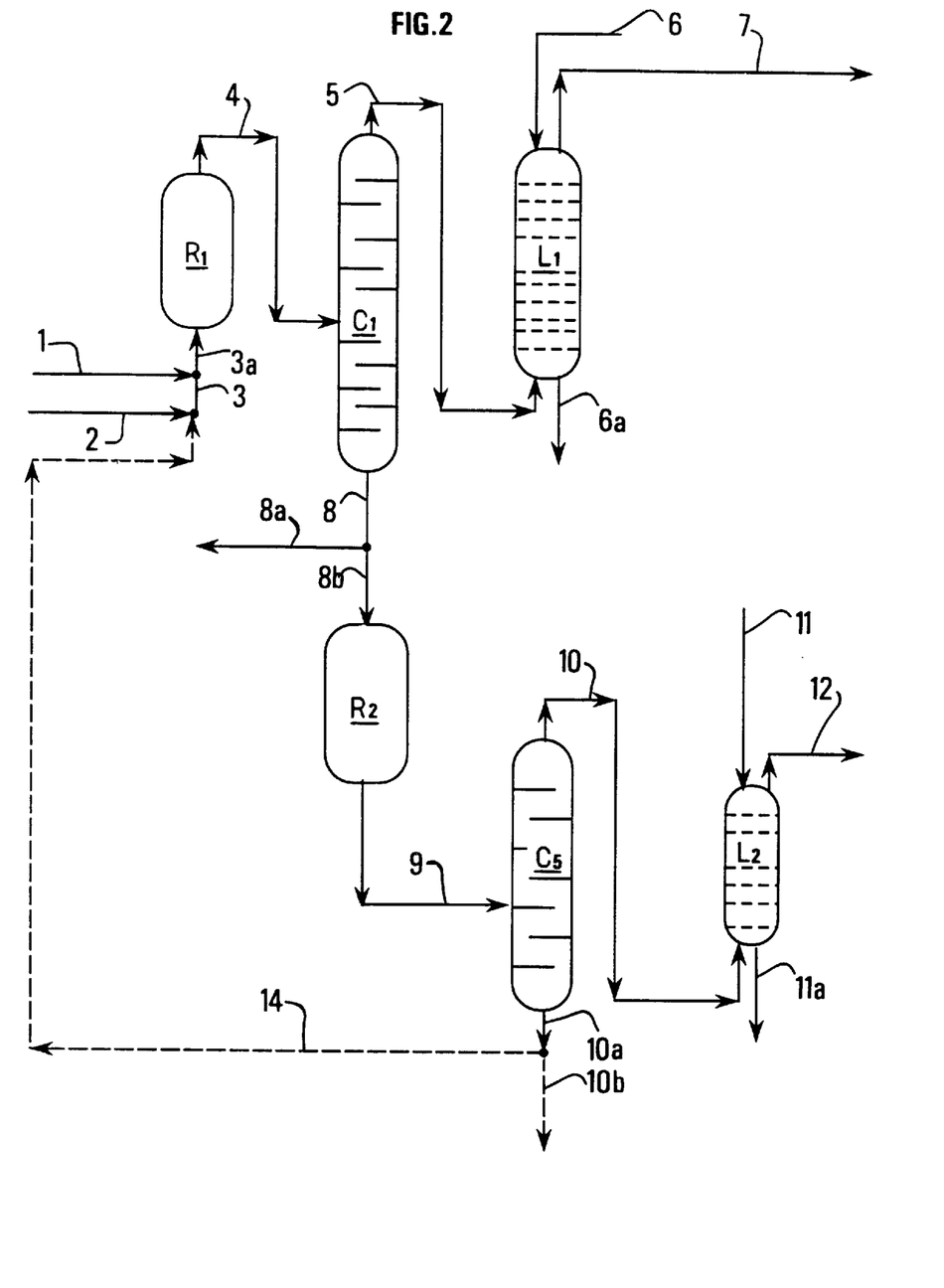

In a variation enabling the purity of the desired olefins to be further increased (see FIG. 2 in particular), the process of the present invention comprises a step e) in which at least a portion of the organic fraction (O1) from the fractionation zone (C1) of step b) is sent via line 5 to a water washing extraction zone (L1) into which the water required for washing is introduced via line 6. In step e), an aqueous fraction (H1) containing water and the major portion of the alcohol initially present in that portion of product (O1) is obtained from this water washing extraction zone (L1) via line 6a and a fraction (O2) containing the major portion of the alpha olefin initially present in said portion of product (O1) is obtained via line 7, said fraction (O2) containing the purified alpha olefin (αhp1), water, and possibly other hydrocarbon compounds originating primarily from the hydrocarbon cut and being substantially free of alcohol. Fraction (H1) can be sent to a water treatment section.

Within the context of the process of the present invention (see FIG. 2 in particular), complementary to or separate from the variation described above, the process of the invention includes a step f) in which at least a portion of the organic fraction (B1) from fractionation zone (C5) of step d) is sent via line 10 to a water washing extraction zone (L2) into which the water required for washing is introduced via line 11. In step f, an aqueous fraction (H2) containing water and the major portion of the alcohol initially present in said portion of product (B1) is obtained from this water washing extraction zone (L2) via line 11a and a fraction (B2) containing the major portion of the tertiary olefin initially present in that portion of product (B1) is obtained via line 12, fraction (B2) containing the purified tertiary olefin (Ohp1), water, possibly light compounds and being substantially free of alcohol. Fraction (H2) can be sent to a water treatment section.

Figure 3:
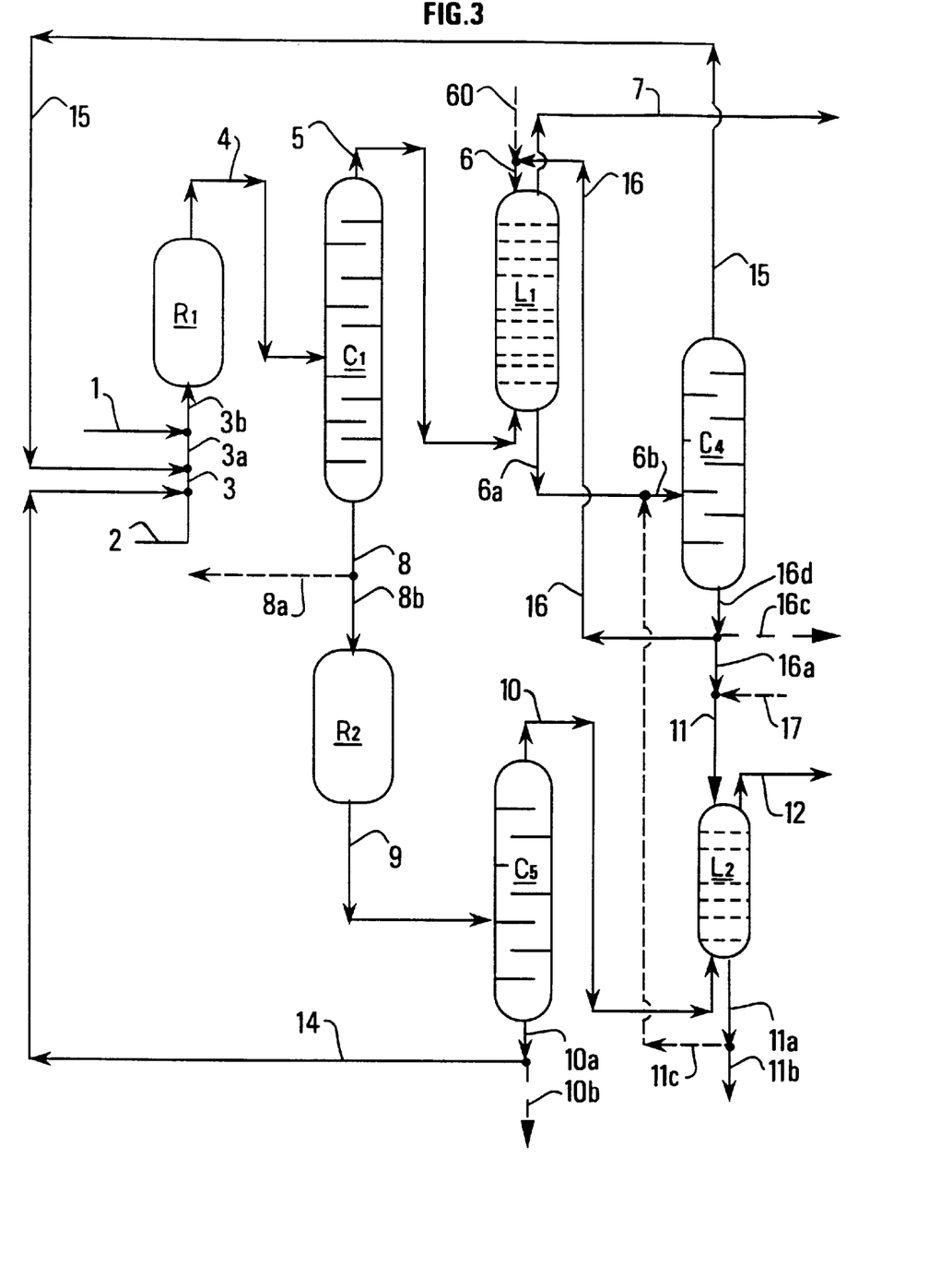

In a further variation (see FIG. 3 in particular), where a portion of fraction (H1) obtained from step e) is used, where at least one of the following zones is present: a zone (L1) carrying out step e) and a zone (L2) carrying out step f), the process of the present invention comprises a step g) in which at least a portion of the aqueous fraction (H1) obtained from step e) (respectively (H2), obtained from water washing extraction step f) from zone (L1) (respectively L2)) is sent via lines 6a and 6b (FIG. 3) to a fractionation zone (C4) to obtain an aqueous fraction (H3) which is depleted in alcohol which is recovered via line 6d and then sent at least in part or in its entirety via lines 16d, 16 and 6 to water washing extraction zone (L1) of step e) and/or at least in part or in its entirety via lines 16d, 16a and 11 to optional zone (L2) (present in FIG. 3) of water washing extraction of step f) and a fraction (A2) which is enriched in alcohol, at least part of which can be returned to etherification zone (R1) of step a) via lines 15, 3a and 3b. In one variation, it is possible to send at least a portion of the aqueous fraction (H3) to a water treatment zone via lines 16d and 16c. In this implementation, makeup water required for washing can be introduced into water washing extraction zone (L1) via lines 60 and 6 and the makeup water required for washing can be introduced into the optional water washing extraction zone (L2) via lines 17 and 11. In this implementation, it is also possible to recycle at least a portion or all of the aqueous fraction (H2), when a zone (C2) carrying out step f) is present, via lines 11a, 11c and 6b into fractionation zone (C4) of step g) and/or to recover at least part or all of this aqueous fraction (H2) via lines 11 and 11b which are sent to a water treatment zone.

In a further variation (see FIG. 4 in particular), when a zone (L1) carrying out step e) is present, the process of the present invention comprises a step h) in which at least a portion of the fraction (O2) from zone (L1) of step e) containing purified alpha olefin (αhp1), water, and possibly light compounds is sent via line 7 to a fractionation zone (C2), from which a fraction (O3) containing high purity alpha olefin (αhp2) is obtained via lines 19 and 90. A fraction (O5) which is depleted in alpha olefin is also obtained from this fractionation zone (C2), via line 18, generally containing one or more linear internal olefins (for example 2-butene in the case of a $C_4$ cut) and linear compounds which are usually saturated (for example butane in the case of a $C_4$ cut). It is possible to send at least a portion, preferably all, of fraction (O3) to a separation zone (D1) via lines 19, 91 and 91a from which a fraction constituted mainly by water is recovered via line 21, and an essentially organic liquid fraction is recovered via line 20 at least part of which is sent as a reflux via line 20a to column C2. Usually, at least a portion of the essentially organic liquid fraction which contains high purity alpha olefin (αhp2) is recovered via line 20 and 22. In this implementation, line 91 then 91a include a condenser to liquefy at least a portion, preferably all, of fraction (O3). When this fraction is not liquefied completely, the remaining gaseous fraction is evacuated from separation zone (D1) via a line which is not shown in FIG. 4. The gaseous fraction is, for example, partly flared off. The aqueous fraction recovered via line 21 can, for example, be returned in part to a water extraction zone of the present process.

In a filter implementation of this variation (see FIG. 4 in particular), the process of the present invention farther comprises a step i) in which at least a portion of the essentially organic liquid fraction containing high purity alpha olefin (αhp2) is sent via line 22 to a fractionation zone (C3) from which a hydrocarbon fraction (O6) containing saturated compounds (paraffins) depleted in alpha olefin is obtained via line 24 and an organic fraction (O4) containing essentially ultra pure alpha olefin (αhp3) is obtained via line 23.

In a further variation (see FIG. 4 in particular), when a zone (L2) carrying out step f) is present, the process of the present invention comprises a step j) in which at least a portion of fraction (B2) containing the purified tertiary olefin (Ohp1), water, and possibly light compounds from zone (L2) is sent via line 12 to a fractionation zone (C6) from which a fraction (B3) containing the high purity tertiary olefin (Ohp2) is recovered via line 25. A fraction (B4) which is depleted in tertiary olefin, generally containing light compounds (such as dimethylether, a small quantity of water and a little isobutene) is also obtained from this fractionation zone, via lines 26 and 200. It is possible to send at least a portion, preferably all, of fraction (B4) via lines 26, 201 and 201a to a separation zone D2 from which a fraction, the major portion of which is constituted by water, is recovered via line 29 and an essentially organic liquid fraction is recovered via line 28 and returned at least in part as a reflux via line 28 to column (C6). In this implementation, line 201 then 201a include a condenser enabling at least a portion of fraction (B4) to be liquefied. The gaseous fraction is evacuated from separation zone (D2) via line 27. The gaseous fraction can for example, be at least partially flared off. The aqueous fraction recovered via line 29 can, for example, be returned at least in part to a water extraction zone of the present process.

Figure 5:
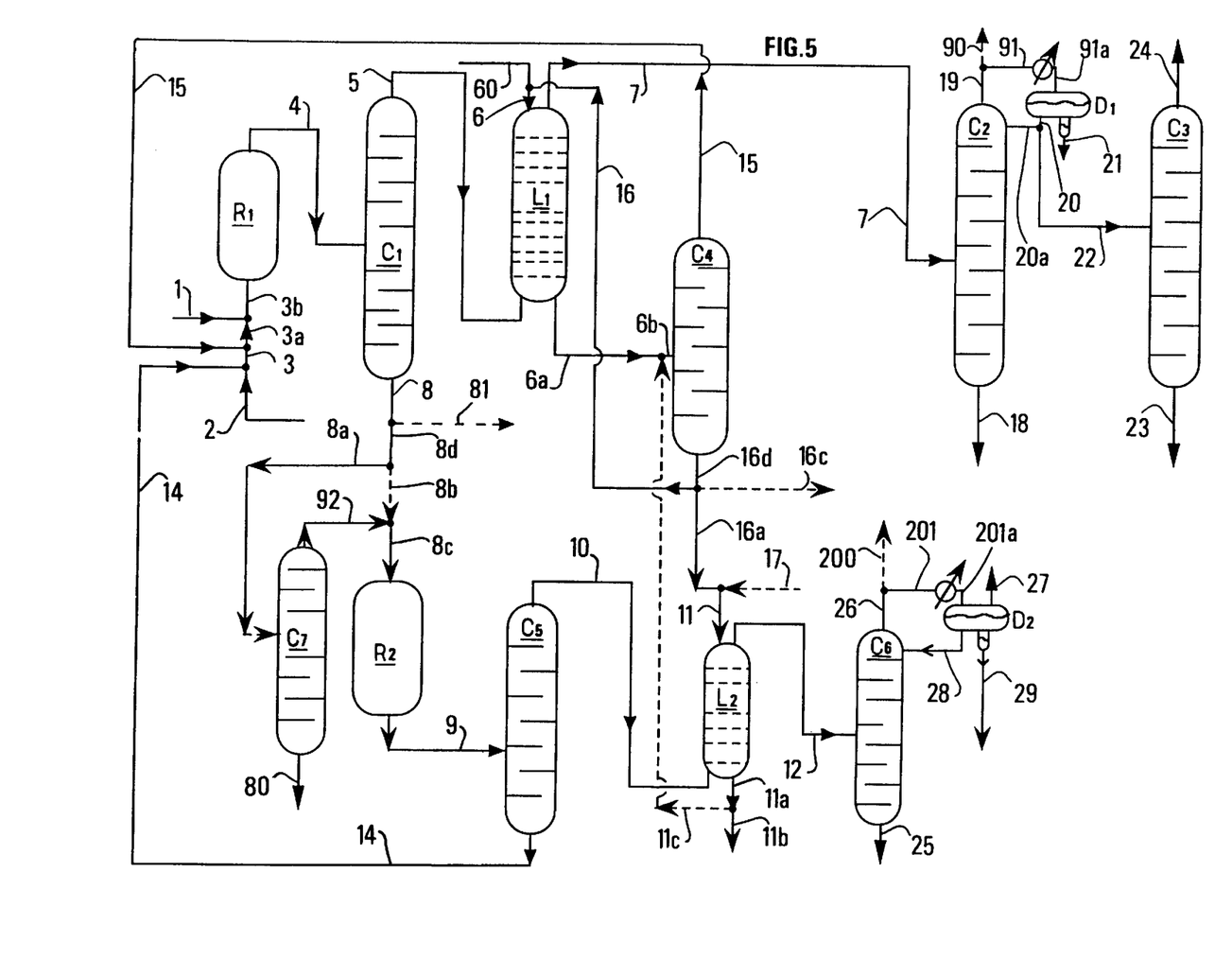

In a further variation (see FIG. 5 in particular), the process of the present invention comprises a step k) in which at least a portion of fraction (E1) from zone (C1) carrying out step b) is sent via lines 8, 8d and 8a to a fractionation zone (C7) from which a fraction (E2) which is enriched in tertiary alkyl ether and depleted in heavy compounds is recovered via line 92 and a fraction (Q) which is depleted in tertiary alkyl ether and enriched in heavy compounds (for example dimers of isobutene and MSBE when treating a $C_4$ cut) is recovered via line 80. This fraction (Q) can be sent to the gasoline pools or eliminated, for example by flaring off. Fraction (E2) is normally sent at least in part via lines 92 and 8c to the tertiary alkyl ether decomposition zone (R2) of step c). When a portion only of fraction (E1) is sent to step k), the other portion can be introduced into the ether decomposition zone of step c) via lines 8b and 8c, preferably mixed with at least a portion of fraction (E2). In a variation, a portion of fraction (E1) can also be sent to the gasoline pools via lines 8 and 81. In the present variation, it is also possible to recover at least a portion of fraction (E2) containing the purified tertiary alkyl ether which can then optionally be sent to the pools or used for other uses.

The conditions under which step a) of the present invention are carried out are conventional conditions which are well known to the skilled person for synthesising a tertiary alkyl ether from a hydrocarbon cut containing at least one tertiary olefin which is etherifiable by at least one alcohol, in particular an alcohol containing 1 to 6 carbon atoms per molecule, usually methanol or ethanol. Ether synthesis is usually carried out in the presence of an acid catalyst, usually a solid acid catalyst selected from the group formed by organic acidic resins (for example sulphonic resins) and mineral acid resins which are generally solid under the ether synthesis reaction conditions (for example grafted mineral solids comprising at least one organic sulphonic group, for example an alkylsulphonic, arylsulphonic, or alkylarylsulphonic group, in particular grafted polysiloxanes and more particularly those grafted with at least one alkylsulphonic group). The catalyst can be a commercial resin such as Amberlyst 15 or 35 resin from ROHM & HAAS or M 31 resin from DOW-CHEMICAL, or a commercially available grafted polysiloxane. In step a), the quantity of alcohol used in normally such that the alcohol/tertiary olefin molar ratio present in the feed is about 0.5:1 to about 8:1, usually 0.8:1 to about 5:1, more usually about 0.9:1 to about 4:1. The reaction temperature is normally about 20° C. to about 120° C., usually about 30° C. to about 100° C., more usually about 40° C. to about 90° C. The HSV (hourly space velocity), the volume of feed per volume of catalyst per hour, is normally about 0.005 to about 100, usually about 0.01 to about 50 and more usually about 0.1 to about 10. The pressure is normally selected so that the constituents present in the reaction zone are in the liquid state. The absolute pressure in this etherification zone is about 1 bar to about 40 bar, normally about 1 bar to about 25 bar (1 bar equals 0.1 MPa).

The conditions for implementing step b) for separating the product from step a) into an organic fraction (O1) containing practically no tertiary alkyl ether and an organic fraction (E1), preferably containing practically all of the tertiary alkyl ether formed during step a), are conventional conditions which depend on the compounds present in the product from step a). This separation can be carried out under conditions of varying severity to obtain a fraction (O1) still containing a small proportion of ether. The skilled person will be able to select the operating conditions to obtain the desired separation. The conditions are usually selected so as to obtain a fraction (E1) containing almost all of the ether formed during step a). Within the context of the invention, the etherification reaction zone of step a) can be distinct from the separation or fractionation zone of step b), or an apparatus can be used which comprises a mixed reaction and fractionation zone (catalytic distillation column) such as that described in a number of prior art patents and other publications. It is normally desirable for the etherification zone to be composed of a principal reaction section and at least one finishing reaction section, the latter preferably comprising either a reactor containing a fixed bed of catalyst or a reactive column (distillation - reaction column), or a combination of the two. The process of the present invention can comprise the use of a reactive distillation zone regrouping the functions of step a) and those of step b), i.e., simultaneously carrying out step a) and step b) of the process of the invention, or using an apparatus comprising at least one reactive distillation column to carry out these steps.

In the case of a process in which MTBE is produced in step a), the separation zone which is generally a distillation separation column normally operates at an absolute pressure of about 1 to about 30 bar, identical to or different from that prevailing in the etherification zone (R1). This column normally comprises 3 to 80 theoretical plates, usually 10 to 50 theoretical plates. A is preferred implementation of the invention comprises an etherification zone comprising at least one etherification reactor (R1) and a fractionation zone comprising a catalytic distillation column containing an etherification catalyst in which etherification is carried out while carrying out distillation to separate an ether fraction and an alpha olefin fraction.

The conditions under which step c) of the present invention are carried out are conventional tertiary alkyl ether decomposition conditions which are well known to the skilled person. In a preferred implementation, this step c) is carried out without adding supplementary water to the product introduced into the decomposition zone. However, it is possible to add a certain quantity of water, for example up to the limit of the solubility of water in the ether which is to be decomposed. Normally, the conditions under which step c) is carried out in zone (R2) are selected so that the major portion of the tertiary alkyl ether decomposes to produce an alcohol and a tertiary olefin. In this zone (R2), the absolute pressure is normally about 1 to about 30 bars, preferably about 1 to about 12 bars, the temperature is normally in the range 50° C. to 300° C. preferably in the range 100° C. to 250° C., and the HSV (hourly space velocity) depends on the catalyst used. In this zone (R2), any of the acid catalysts known to the skilled person can be used. Solid acid catalysts are preferably used. Thus the catalyst can be selected from the group formed by organic acid resins and mineral acid resins which are generally solids under the ether decomposition reaction conditions. Of these compounds, those selected from the group formed by grafted mineral solids containing at least one alkylsulphonic, arylsulphonic or alkylarylsulphonic type organic group are usually used. In one preferred implementation of this step c), a catalyst selected from the group formed by polysiloxanes grafted with at least one alkylsulphonic group is used.

The general conditions for carrying out step d) for fractionating product (P1) from step c) in fractionation zone (C5) are selected as a function of the characteristics of the alcohol and tertiary olefin formed. The skilled person is able to select the conditions so as to obtain the desired separation between a fraction containing the major portion of the alcohol and a fraction containing the major portion of the olefin. Thus, for example, in the case of MTBE decomposition and the formation of methanol and isobutene, the absolute pressure in zone (C5) which is a distillation column is about 1 to about 15 bar, preferably about 1 to about 10 bar, identical to or different from that prevailing in decomposition zone (R2). The column bottom temperature depends both on the pressure prevailing in the column and the composition of the bottoms product, in particular the molar ratio between the methanol and the MTBE which may be present following partial decomposition of this ether in step c). for a unit treating 1 kg/h of MTBE, the distillation column normally comprises between 3 and 80 theoretical plates, usually between 10 and 50 theoretical plates.

In optional purification step e), at least a portion of fraction (O1) containing the major portion of the alpha olefin obtained in step b) is sent to a water washing extraction zone (L1). The quantity of water used for washing is normally such that the ratio between the volume of that quantity of water introduced into the extraction zone and that of the portion of product (O1) introduced into the extraction zone ($V_{water}/V_{O1}$) is about 0.005 to about 20 by volume. This quantity of water is usually such that the ratio $V_{water}/V_{O1}$ is about 0.005 to about 10, preferably about 0.01 to about 5, more preferably about 0.02 to about 1. The water flow rate in this washing zone (L1) is usually regulated so as to maintain a foundation level in the water and alcohol fractionation zone (C4) when such a zone (C4) is present carrying out step g). This foundation level can be defined as the minimum level required for fractionation zone (C4) to operate properly. This parameter is a conventional parameter which is well known to the skilled person. The regulation is often carried out manually by the operators, but it is possible for this regulation to be carried out by an automatic Level Control Regulation circuit. Regardless of the selected mode of regulation, the quantity of water is generally adjusted using a means for introducing makeup water into water washing zone (L1) of step e). This makeup water can in particular compensate for loss of water due to entrainment and/or saturation of the treated hydrocarbon stream and can replace any purged water. This extraction zone (L1) is normally a tray column which operates at a temperature of about 1° C. to about 100° C., preferably about 10° C. to about 60° C. The absolute pressure in this zone is about 1 to about 20 bars, normally about 1 to about 15 bars, identical to or different from that prevailing in fractionation zone (C1) of step b).

In optional purification step f), at least a portion of fraction (B1) containing the major portion of the tertiary olefin obtained in step d) is sent to a water washing extraction zone (L2). The quantity of water used for washing is normally such that the ratio between the volume of that quantity of water introduced into the extraction zone and that of the portion of product (B1) introduced into the extraction zone ($V_{water}/V_{B1}$) is about 0.005 to about 20 by volume. This quantity of water is usually such that the ratio $V_{water}/V_{B1}$ is about 0.005 to about 10, preferably about 0.01 to about 5, more preferably about 0.02 to about 1. The water flow rate in this washing zone (L1) is usually regulated so as to maintain a foundation level in the water and alcohol fractionation zone (C6) when such a zone (C6) is present carrying out step g). This foundation level can be defined as the minimum level required for fractionation zone (C6) to operate properly. This parameter is a conventional parameter which is well known to the skilled person. The regulation is often carried out manually by the operators, but it is possible for this regulation to be carried out by an automatic Level Control Regulation circuit. Regardless of the selected mode of regulation, the quantity of water is generally adjusted using a means for introducing makeup water into water washing zone (L2) of step f). This makeup water can in particular compensate for loss of water due to entrainment and/or saturation of the treated hydrocarbon stream and can replace any purged water. This extraction zone (L2) is normally a tray column which operates at a temperature of about 1° C. to about 100° C., preferably about 10° C. to about 60° C. The absolute pressure in this zone is about 1 to about 20 bars, normally about 1 to about 15 bars, identical to or different from that prevailing in fractionation zone (C5) of step d).

Optional step g), when a zone (L1) carrying out step e) and/or a zone (L2) carrying out step f) are present, for fractionation of at least a portion of the aqueous fraction(s) (H1) and/or (H2), containing the major portion of the alcohol initially present in the fraction (and/or in the mixture of fractions) (H1) recovered from optional water extraction zone (L1) of step e) and/or (H2) recovered from optional water extraction zone (L2) of step f), in which at least a portion of the mixture of fractions or fraction (H1) and/or (H2) is separated into a fraction (A2) containing the major portion of the alcohol initially present in said portion of the mixture or said fraction (H1) and/or (H2) and an aqueous fraction (H3) which is free of the major portion of the alcohol initially present in said portion of said mixture of fractions or said fraction (H1) and/or (H2), is normally carried out in a fractionation zone (C4) which is generally a distillation column (C4) at an absolute pressure of about 1 to about 12 bar, preferably about 1 to about 8 bar, identical to or different from that prevailing in water extraction zones (L1) and/or (L2) of step e) and step f). The column bottom temperature particularly depends on the pressure in the column, and is normally about 50° C. to about 300° C., usually about 65° C. to about 200° C. The column normally comprises about 2 to about 80 theoretical plates, usually about 3 to about 60 theoretical plates.

Optional step h) for fractionating at least a portion of fraction (O2) from zone (L1), when such a zone (L1) carrying out step e) is present, into a fraction (O3) containing the purified tertiary olefin (αhp2), residual water contained in the liquid fraction (O2) and light compounds, and into a fraction (O5) containing the major portion of the saturated compounds and linear internal olefins which may be present in said portion of fraction (O2) is normally carried out in a fractionation zone (C2) which is generally a distillation column operating at an absolute pressure of about 1 to about 15 bar, usually about 3 bar to about 10 bar, identical to or different from that prevailing in extraction zone (L1) of step e). For a unit producing 0.3 kg/h of 1-butene, the column normally has about 3 to about 100 theoretical plates, usually about 10 to about 70 theoretical plates. The column bottom temperature depends in particular on the pressure in the column.

Optional step i) for fractionating at least a portion of fraction (O3) from zone (C2), when a zone (L1) carrying out step e) is present and a zone (C2) carrying out step h) is present, into a fraction (O4) containing purified tertiary olefin (αhp3), and into a fraction (O6) containing the major portion of the saturated compounds which may be present in said portion of fraction (O3), is normally carried out in a distillation column operating at an absolute pressure of about 1 to about 15 bar, usually about 3 bar to about 10 bar, identical to or different from that prevailing in fractionation zone (C2) of step h). For a unit producing 0.3 kg/h of 1-butene, the column normally has about 3 to about 80 theoretical plates, usually about 5 to about 50 theoretical plates. The column bottom temperature depends in particular on the pressure in the column.

Optional step j) for fractionating at least a portion of fraction (B2) from zone (L2), when a zone (L2) carrying out step f) is present, into a fraction (B3) containing purified tertiary olefin (Ohp2) and into a fraction (B4) containing the major portion of the light compounds which may be present in said fraction (B2) and residual water contained in said portion of liquid fraction (B2), is normally carried out in a fractionation zone (C6) which is generally a distillation column operating at an absolute pressure of about 1 to about 15 bar, usually about 3 bar to about 10 bar, identical to or different from that prevailing in extraction zone (L2) of step f). For a unit producing 0.6 kg/h of isobutene, the column normally has about 3 to about 80 theoretical plates, usually about 5 to about 50 theoretical plates. The column bottom temperature depends in particular on the pressure in the column.

In a particular implementation which can further improve the process of the present invention, at least a portion of the organic fraction(s) containing the desired olefin(s) obtained from the outlet from at least one water washing extraction zone (L1) or (L2) when at least one such zone (L1) or (L2) is present, which is associated with a zone (C2), zone (L1) being associated with zone (C2) carrying out step h) of the invention and zone (L2) being associated with zone (C6) carrying out step j) of the invention, is (are) sent to a separation zone (Coe) from which an aqueous liquid fraction (Lae) is recovered and an organic liquid fraction (Lbe) containing the major portion of the olefin initially present in said portion is recovered; said fraction (Lbe), which is depleted in water and which contains the olefin and possibly other compounds, is then sent respectively to the fractionation zone (C2) when zone (L1) is present and (C6) when zone (L2) is present from which purified alpha olefin (α'hp2) and purified tertiary olefin (O'hp2) are respectively obtained. This implementation which comprises a zone for separating an aqueous liquid fraction (Lae) and an organic liquid fraction (Lbe) is normally carried out in an apparatus termed a coalescer, in which water collects in the lower portion of the apparatus by coalescence. The temperature and pressure conditions in this zone are in the same ranges as those in the corresponding and preceding water extraction step. The pressure (or, respectively, the temperature) can be identical to or different from that in the preceding step. In this zone (Coe), free water contained in the product from the water extraction step is separated out. Further, the zone also acts as a feed zone or drum for the subsequent olefin purification zone. Any other known means can be used within the context of the present invention. As an example, the use of an absorbent with preferential selectivity for the aqueous or the organic fraction can be used.

The following example illustrates the invention without limiting its scope.

EXAMPLE

A pilot type unit was used which comprised three tube reactors (R1), (R2) and (R3) to carry out the ether synthesis and decomposition reaction steps. The first reactor (R1) had a volume of 20 milliliters and contained 6 grams of Amberlyst 15 resin sold by ROHM & HAAS and operated at a relative pressure of 10 bar, at an average temperature of 50° C. It was supplied with a $C_4$ cut from catalytic cracking containing 20% by weight of isobutene and 20% by weight of 1-butene, and by pure methanol sold by ALDRICH as a product with a purity of over 99% by weight. The quantity of methanol was adjusted so that the methanol/isobutene molar ratio introduced into reactor (R1) was 1.2. The reactor operated at an HSV of 0.5 $h^{-1}$. Under the selected conditions, conversion of isobutene to MTBE was 97%. The effluent from R1 was taken up in a second etherification step comprising a reactor R2 with identical characteristics to those of reactor R1 and containing the same catalyst in an identical quantity, operating under the same conditions as R1. 95% of the isobutene not converted in R1 was then transformed into MTBE in R2. Over the R1 and R2 ensemble, an overall isobutene to MTBE conversion of 99.8% was obtained.

The second reactor (R3) with a volume of 10 milliliters contained 3 grams of commercially available catalyst based on polysiloxanes grafted with at least one alkylsulphonic group. Reactor (R3) was supplied with a feed containing 100% by weight of MTBE, at an HSV of 15 $h^{-1}$, the relative pressure in the reactor was 7 bar and the average temperature was 160° C. Table 1 shows the composition of the feed introduced into MTBE decomposition reactor (R3) and the composition of the product recovered from the outlet from reactor (R3).

TABLE 1

|  | Feed (wt %) | R3 effluent (wt %) |
|---|---|---|
| MTBE | 100 | 10 |
| Isobutene |  | 56.1 |
| Methanol |  | 32.1 |
| DME |  | 0.5 |
| Dimers |  | 1.1 |
| $H_2O$ |  | 0.2 |

The various purification sections were calculated using software produced by American company SIMSCI (SIMulation SCIence INC.) under the trade name Pro II.

A distillation column (C1), operating at a relative pressure of 7 bar, comprising 10 theoretical plates, was used in step b) of the process of the invention to obtain a bottoms product (E1) and an overhead product (O1). (This simulated fractionation of the product from step a) for etherification of the isobutene contained in the $C_4$ cut).

A distillation column (C5), operating at a relative pressure of 7 bar, comprising 30 theoretical plates, was used in step d) of the process of the invention to obtain a bottoms product (A1) and an overhead product (B1). (This simulated the isobutenemethanol fractionation of the product from MTBE decomposition step c)).

A water washing extraction column (L2), a tray column operating at a temperature of 30° C., was used in step f) of the process of the invention to obtain an aqueous fraction (H2) and an organic fraction (B2). (This simulated extraction of residual methanol from fraction (B2) from step d) which fractionated the product from MTBE decomposition step c)).

A coalescer type (Co2) system for extracting entrained free water was used in step f) for fraction (B2), enabling an aqueous fraction (La2) and an organic fraction (Lb2) to be obtained. It operated at a relative pressure of 12 bar and a temperature of 30° C.

A distillation column (C6), the last step in the isobutene purification, operating at a relative pressure of 7 bars and comprising 25 theoretical plates, was used in step j) of the process of the invention to obtain a bottoms product (B3) which was purified isobutene (Ohp3) and an overhead product (B4) containing light compounds.

A water washing extraction column (L1), a tray column operating at a temperature of 30° C., was used in step e) of the process of the invention to obtain an aqueous fraction (H1) and an organic fraction (O2). (This simulated extraction of residual methanol from fraction (O1) from step b) for fractionation of the product from etherification step a)).

A coalescer type (Co1) system for extracting entrained free water in step e) for fraction (O2), enabling an aqueous fraction (La1) and an organic fraction (Lb1) to be obtained. It operated at a relative pressure of 12 bar and a temperature of 30° C.

A distillation column (C2) for purification of the organic fraction (Lb1) which operated at a relative pressure of 7 bar and comprising 20 theoretical plates was used in step h) of the process of the invention to obtain an overhead product (O3) which was purified 1-butene (αhp2) and a bottoms product (O5) containing $C_4$ compounds other than isobutene and 1-butene.

A distillation column (C3) for purification of the organic fraction (O3) which operated at a relative pressure of 7 bar, comprising 20 theoretical plates was used in step i) of the process of the invention to obtain an overhead product (O6) containing isobutane and a bottoms product (O4) which was very high purity 1-butene (αhp3).

Column (C1) was supplied with the product from etherification reactor (R2). Product (E1) recovered from the bottom of column (C1) was used to supply reactor (R3). Product (O1) recovered overhead from C1 was sent to a water washing extraction zone (L1) from which a product (O2) containing purified 1-butene (αhp1) was obtained. Column C5 was supplied with effluent P1 from R3. Product B1 recovered overhead from C5 was sent to an extraction column L2 where it was washed with a certain quantity of water. An aqueous fraction H2 containing the major portion of the methanol contained in B1 and a hydrocarbon fraction B2 containing a small quantity of entrained free water were recovered. This fraction of free water was finally eliminated after decanting in decanting system Co2. Finally, the hydrocarbon fraction Lb2 was treated in column C6 to produce a fraction B3 from the bottom which was essentially high purity isobutene (Ohp3) and a light fraction B4 overhead containing dimethylether (DME) in particular.

The material balances obtained are given in Tables 2, 3, 4 and 5 below. Table 2 shows the material balance relative to the two first MTBE synthesis reaction steps. Tables 3 and 4 show the material balance relative to MTBE decomposition and the production of high purity isobutene. Table 5 shows the material balance relative to purification of 1-butene.

TABLE 2

|  | Feed R1 (wt) | Effluent R1 (wt) | Effluent R2 (wt) | Head C1 (wt) | Bottom C1 (wt) |
|---|---|---|---|---|---|
| Isobutene | 20 | 0.6 | 0.03 | 0.03 |  |
| 1-butene | 20 | 20 | 20 | 20 |  |
| C4 ex isobutene | 60 | 60 | 60 | 60 |  |
| Methanol | 13.7 | 2.7 | 2.37 | 2.37 |  |
| MTBE | 0 | 30.4 | 31.3 | 0 | 31.3 |
| Total | 113.7 | 113.7 | 113.7 | 82.4 | 31.3 |

TABLE 3

|  | Effluent R3 | Bottom C5 fraction A1 (g/h) | Head C5 fraction B1 (g/h) | Washing water column L2 | Aqueous fraction H2 column L2 | Organic fraction B2 column L2 |
|---|---|---|---|---|---|---|
| MTBE | 10 | 10 |  |  |  |  |
| Isobutene | 56.1 |  | 56.1 |  |  | 56.1 |
| Methanol | 32.1 | 30.4 | 1.7 |  | 1.7 |  |
| DME | 0.5 |  | 0.5 |  |  | 0.5 |
| Dimers | 1.1 | 1.1 |  |  |  |  |
| $H_2O$ | 0.2 |  | 0.2 | 10 | 9.2 | 1 |
| Flow rate (g/h) | 100 | 41.5 | 58.5 | 10 | 10.9 | 57.6 |

TABLE 4

|  | Aqueous fraction La2 extracted by Co2 | Organic fraction Lb2 extracted by Co2 | Fraction B4 column C6 | Fraction B3 column C6 |
|---|---|---|---|---|
| Isobutene |  | 56.1 | 1.72 | 54.38 |
| DME |  | 0.5 | 0.49 | 0.01 |
| $H_2O$ | 0.99 | 0.01 | 0.01 |  |
| Flow rate (g/h) | 0.99 | 56.61 | 2.22 | 54.39 |
| Isobutene purity (%) |  |  |  | 99.9% |

TABLE 5

|  | Head C1 (wt) | Fraction O2 column L1 | Fraction O3 column C2 (wt) | Fraction O5 column C2 (wt) | Fraction O6 column C3 (wt) | Fraction O4 column C3 (wt) |
|---|---|---|---|---|---|---|
| Isobutene | 0.03 | 0.03 | 0.03 |  |  | 0.03 |
| 1-butene | 20 | 20 | 20 |  |  | 20 |
| Isobutane | 15 | 15 | 15 |  | 15 |  |
| n-butane | 45 | 45 |  | 45 |  |  |
| 2-butene |  |  |  |  |  |  |

TABLE 5-continued

|  | Head C1 (wt) | Fraction O2 column L1 | Fraction O3 column C2 (wt) | Fraction O5 column C2 (wt) | Fraction O6 column C3 (wt) | Fraction O4 column C3 (wt) |
|---|---|---|---|---|---|---|
| Methanol | 2.37 | | | | | |
| Total | 82.4 | 80.03 | 35.03 | 45 | 15 | 20.03 |

This example shows that carrying out the process of the invention enables an isobutene with a purity of 99.9% and a global conversion of 83% to be obtained from a $C_4$ cut containing 1-butene and isobutene without optimisation, i.e., no recycling, and 1-butene with a purity of 99.85%. The high purity isobutene yield can be improved by using various recycling steps including that of fraction A1 (bottom of column C5).

We claim:

1. A process for the production of a pure alpha olefin, a pure tertiary olefin and optionally a tertiary alkyl ether from an unsaturated hydrocarbon cut containing at least one alpha olefin and at least one etherifiable tertiary olefin, said process being characterized in that it comprises:
   a) a step for forming at least one tertiary alkyl ether by bringing an hydrocarbon cut containing at least one alpha olefin and at least one etherifiable tertiary olefin into contact with at least one alcohol in a reaction zone (R1) containing an etherification catalyst;
   b) a step for fractionating at least a portion of the product from step a) in a fractionation zone (C1) to obtain an organic fraction (O1) which is depleted in tertiary alkyl ether and containing the alpha olefin, and an organic fraction (E1), enriched in the tertiary alkyl ether formed during step a);
   c) a step for decomposing at least a portion of the tertiary alkyl ether contained in the organic fraction (E1) from step b) into a product (P1) containing at least one alcohol and at least one tertiary olefin, in a reaction zone (R2) containing a catalyst for decomposing said ether; and
   d) a step for fractionating at least a portion of product (P1) from step c), in a fractionation zone (C5) to obtain a fraction (B1) containing the major portion of the tertiary olefin and possibly a minor fraction of alcohol and possibly light compounds which may be initially contained in said portion of product (P1), and into a fraction (A1) containing the major portion of the alcohol formed in step c), possibly ether which has not decomposed in step c) and possibly heavy compounds initially contained in said portion of product (P1) from step c).

2. The process according to claim 1, in which at least a portion of fraction (A1) is sent to zone (R1).

3. The process according to claim 1, comprising a step e) in which at least a portion of the organic fraction (O1) from fractionation zone (C1) of step b) is sent to a water washing extraction zone (L1) from which an aqueous fraction (H1) containing water and the major portion of the alcohol initially present in said portion of product (O1) and a fraction (O2) containing the major portion of the alpha olefin initially present in said portion of product (O1) are obtained, said fraction (O2) containing said purified alpha olefin (αhp1), water, and possibly other hydrocarbon compounds and being substantially free of alcohol.

4. The process according to claim 1, comprising a step f) in which at least a portion of fraction (B1) is sent to a water washing zone (L2) from which a fraction (B2) containing the major portion of the tertiary olefin initially present in said portion of product (B1) is recovered, said fraction (B2) containing said purified tertiary olefin (Ohp1), water, and possibly light compounds and being substantially free of alcohol, and an aqueous fraction (H2) containing water and the major portion of the alcohol initially present in said portion of product (B1) is recovered.

5. The process according to claim 3, comprising a step a) in which at least a portion of fraction (H1) from step e) or fraction (H2) from step f) is sent to a fractionation zone (C4) to obtain an aqueous fraction (H3) which is depleted in alcohol and a fraction (A2) which is enriched in alcohol.

6. The process according to claim 5, in which at least a portion of said fraction (A2) is recycled to the ether synthesis zone (R1) of step a).

7. The process according to claim 5, in which at least a portion of the aqueous fraction (H3) is sent to the water extraction zone (L1) of step e) or to water extraction zone (L2) of step f).

8. The process according to claim 3, comprising at least one means for introducing makeup water into the water washing extraction zone (L1) of step e) when such a zone (L1) is present.

9. The process according to claim 4, comprising at least one means for introducing makeup water into the water washing extraction zone (L2) of step f) when such a zone (L2) is present.

10. The process according to claim 3, comprising a step h) when a zone (L1) carrying out step e) is present, in which at least a portion of the organic fraction (O2) from zone (L1) of step e) is sent to a fractionation zone (C2) from which a fraction (O3) containing high purity alpha olefin (αhp2) and a fraction (O5) which is depleted in alpha olefin are obtained.

11. The process according to claim 10, comprising a step i) in which at least a portion of the fraction (O3) is sent to a fractionation zone (C3) from which a fraction (O4) containing high purity alpha olefin (αhp3) and a fraction (O6) containing saturated compounds which are initially present in said portion of fraction (O3) are obtained.

12. The process according to claim 3, in which, when a zone (L2) carrying out step f) is present, at least a portion of fraction (B2) is sent, in a step j), to a fractionation zone (C6) from which a fraction (B3) containing high purity tertiary olefin (Ohp2) and a fraction (B4) which is depleted in tertiary olefin are recovered.

13. A process according to claim 1, comprising a step k) in which at least a portion of fraction (E1) from zone (C1) of step b) containing the tertiary alkyl ether is sent to a fractionation zone (C7) from which a fraction (E2) which is enriched in tertiary alkyl ether and depleted in heavy compounds and a fraction (Q) which is depleted in tertiary alkyl ether and enriched in heavy compounds are recovered.

14. A process according to claim 13, in which at least a portion of fraction (E2) which is enriched in tertiary alkyl ether is sent to step c) to zone (R2) for decomposition of said tertiary alkyl ether.

15. A process according to claim 13, in which at least a portion of the organic fraction (E1) is sent to the motor fuel pool and a further portion of said organic fraction (E1) is sent to fractionation step k).

16. A process according to claim 1, in which the fractionation zone (C1) comprises a reactive distillation zone carrying out step a) and step b) of said process simultaneously.

17. A process according to claim 3, in which as least a portion of the organic fraction(s) obtained from the outlet from at least one water washing extraction zone (L1) is sent to a separation zone (Coe) from which an aqueous liquid fraction (Lae) is recovered and an organic liquid fraction (Lbe) containing the major portion of the olefin initially present in said portion is recovered; said fraction (Lbe) being depleted in water and containing said olefin and possibly other compounds, then being sent to fractionation zone (C2) from which purified alpha olefin ($\alpha$'hp2) is obtained.

18. A process according to claim 4, wherein at least a portion of the fractions obtained from the outlet of at least one water washing extraction zone (L2) is sent to a separation zone (Coe) from which an aqueous liquid fraction (Lae) is recovered and an organic liquid fraction (Lbe) containing the major portion of the olefin initially present in said portion is recovered; said fraction (Lbe) being depleted in water and containing said olefin and possibly other compounds, then being sent to fractionation zone (C6) from which purified tertiary olefin (O'hp2) is obtained.

* * * * *